United States Patent
VanGompel et al.

(10) Patent No.: US 6,387,084 B1
(45) Date of Patent: *May 14, 2002

(54) SANITARY NAPKIN WITH GARMENT ATTACHMENT PANELS

(75) Inventors: Paul Theodore VanGompel, Hortonville; Julie Terese Brocker, Appleton; Lori Sue Schutkoske, Winneconne; Betsy Carolyn Westlake, Appleton, all of WI (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/600,317

(22) Filed: Feb. 13, 1996

Related U.S. Application Data (63) Continuation of application No. 08/255,843, filed on Jun. 8, 1994, now abandoned, which is a continuation of application No. 07/954,524, filed on Sep. 30, 1992, now abandoned.

(51) Int. Cl.$^7$ .............................................. A61F 13/15
(52) U.S. Cl. .................... 604/385.04; 604/387
(58) Field of Search .............................. 604/385.1, 386, 604/387, 389, 390, 391, 385.03, 385.04, 385.05

(56) References Cited

U.S. PATENT DOCUMENTS

| | | |
|---|---|---|
| 75,434 A | 3/1868 | Libbey |
| 462,974 A | 11/1891 | Allen |
| 478,053 A | 6/1892 | Dyer |
| 791,354 A | 5/1905 | Merkley |
| 830,757 A | 9/1906 | Williams |
| 867,091 A | 9/1907 | Altermatt |
| 924,337 A | 6/1909 | Frommann |

(List continued on next page.)

FOREIGN PATENT DOCUMENTS

| | | |
|---|---|---|
| AU | 788166 | 7/1966 |
| AU | B3026584 | 7/1984 |
| AU | A3027484 | 9/1984 |

(List continued on next page.)

OTHER PUBLICATIONS

Takatoshi Kobayashi; Utilization of water–absorbent polymers in hygienic field; Zairyo Gijutsu, 6(9), 361–365 (1988)
Notice of Opposition of McNeil–PPC, Inc., to the grant of European Patent Application 93115757.2, filed Jan. 30, 1998.
Notice of Opposition of SCA Mölnlycke AB, to the grant of European Patent Application 93115757.2, filed Feb. 2, 1998.

(List continued on next page.)

Primary Examiner—Dennis Ruhl
(74) Attorney, Agent, or Firm—Brinks Hofer Gilson & Lione (57) ABSTRACT

An elongated sanitary napkin has deflectable longitudinal side edges formed by an edge or peripheral seal along the opposite sides of an absorbent. A garment attachment panel is secured to the underside of each side edge. A fixed portion of the panel is bonded flat against the side edge so that a free portion of the panel, extending from the fixed portion, is directed inward and downward. During use, the panels are fastened together beneath an undergarment crotch portion by hook and loop type fastener. Fastener and panels are sized so that when fastened the panels exert a pull on the side edges, controlling their deflection and, for example, preventing them from folding in over the absorbent. The garment attachment panels confine the undergarment crotch portion under the absorbent so that, for example, an elasticized edge of the crotch portion is prevented from pulling up and onto the absorbent.

10 Claims, 3 Drawing Sheets

U.S. PATENT DOCUMENTS

| | | | |
|---|---|---|---|
| 1,022,894 A | 4/1912 | Sprague | |
| 1,146,245 A | 7/1915 | Goldman | |
| 1,386,936 A | 8/1921 | Kirwan | |
| 1,653,857 A | 12/1927 | Kelly | |
| 1,664,298 A | 3/1928 | Katz | |
| 1,837,483 A | 12/1931 | Cecil-Reaney | |
| 1,882,309 A | 10/1932 | Williams | |
| 1,912,783 A | 6/1933 | Meyer | |
| RE18,939 E | 9/1933 | Harrington | |
| 1,975,457 A | 10/1934 | Heyman | |
| 1,975,618 A | 10/1934 | Raskin | |
| 2,026,158 A | 12/1935 | Bennett | |
| 2,076,526 A | 4/1937 | Brown | |
| 2,154,332 A | 4/1939 | Hirsch | |
| 2,295,016 A | 9/1942 | Scribner | |
| 2,408,508 A | 11/1946 | Canavan | |
| 2,636,494 A | 4/1953 | Hon | |
| 2,787,271 A | 4/1957 | Clark | |
| 2,840,078 A | 6/1958 | Smith | |
| 2,890,701 A | 6/1959 | Weinman | |
| 3,070,095 A | 12/1962 | Torr | |
| 3,096,765 A | 7/1963 | Cornwell | |
| 3,315,677 A | 4/1967 | Tyrrell | |
| 3,342,184 A | 9/1967 | Joa | |
| 3,397,697 A | 8/1968 | Rickard | |
| 3,400,718 A | 9/1968 | Saijo | |
| 3,613,686 A | 10/1971 | Woskin | |
| 3,670,731 A | 6/1972 | Harmon | |
| 3,686,024 A | 8/1972 | Nankee et al. | |
| 3,744,494 A | 7/1973 | Marsan | |
| 3,881,490 A | 5/1975 | Whitehead et al. | |
| 3,888,255 A | 6/1975 | Shah et al. | |
| 3,890,974 A | 6/1975 | Kozak | |
| 3,897,783 A | 8/1975 | Ginocchio | |
| 3,913,580 A | 10/1975 | Ginocchio | |
| 3,973,567 A | 8/1976 | Srinivasan et al. | |
| 4,041,203 A | 8/1977 | Brock et al. | |
| 4,055,180 A | 10/1977 | Karami | |
| 4,055,184 A | 10/1977 | Karami | |
| D247,372 S | 2/1978 | Whitehead | |
| 4,144,886 A | 3/1979 | Holst et al. | |
| 4,147,580 A | 4/1979 | Buell | |
| 4,176,667 A | 12/1979 | Herring | |
| 4,217,901 A | 8/1980 | Bradstreet et al. | |
| 4,248,822 A | 2/1981 | Schmidt | |
| 4,280,978 A | 7/1981 | Dannheim et al. | |
| 4,285,343 A * | 8/1981 | McNair | 128/287 |
| 4,324,246 A | 4/1982 | Mullane et al. | |
| 4,327,732 A | 5/1982 | Thinnes | |
| 4,333,465 A | 6/1982 | Wiegner | |
| 4,342,314 A | 8/1982 | Radel et al. | |
| 4,364,992 A | 12/1982 | Ito et al. | |
| 4,425,130 A | 1/1984 | DesMarais | |
| 4,456,570 A | 6/1984 | Thomas et al. | |
| 4,463,045 A | 7/1984 | Ahr et al. | |
| 4,496,359 A | 1/1985 | Pigneul | |
| 4,500,585 A | 2/1985 | Erickson | |
| 4,540,415 A | 9/1985 | Korpman | |
| 4,551,143 A | 11/1985 | Cook et al. | |
| 4,589,876 A | 5/1986 | Van Tilburg | |
| 4,608,047 A * | 8/1986 | Mattingly | 604/387 |
| 4,655,759 A | 4/1987 | Romans-Hess et al. | |
| 4,668,230 A | 5/1987 | Damico et al. | |
| 4,687,478 A * | 8/1987 | Van Tilburg | 604/387 |
| 4,701,177 A | 10/1987 | Ellis et al. | |
| 4,701,178 A * | 10/1987 | Glaug et al. | 604/387 |
| 4,710,189 A | 12/1987 | DeRossett et al. | |
| RE32,649 E | 4/1988 | Brandt et al. | |
| 4,738,676 A | 4/1988 | Osborn, III | |
| 4,755,413 A | 7/1988 | Morris | |
| 4,759,754 A | 7/1988 | Korpman | |
| 4,770,657 A | 9/1988 | Ellis et al. | |
| 4,773,905 A | 9/1988 | Molee et al. | |
| 4,773,906 A * | 9/1988 | Krushel | 604/391 |
| 4,790,838 A | 12/1988 | Pigneul et al. | |
| 4,798,601 A | 1/1989 | Shirose et al. | |
| 4,798,603 A | 1/1989 | Meyer et al. | |
| 4,798,604 A | 1/1989 | Carter | |
| 4,848,572 A | 7/1989 | Herrera | |
| 4,862,574 A | 9/1989 | Seidy | |
| 4,886,513 A | 12/1989 | Mason, Jr. et al. | |
| 4,900,319 A | 2/1990 | Richwine | |
| 4,900,320 A | 2/1990 | McCoy | |
| 4,911,701 A | 3/1990 | Mavinkurve | |
| 4,917,697 A | 4/1990 | Osborn, III et al. | |
| 4,936,839 A | 6/1990 | Molee et al. | |
| 4,940,462 A | 7/1990 | Salerno | |
| 4,964,860 A | 10/1990 | Gipson et al. | 604/391 |
| 5,007,906 A | 4/1991 | Osborn, III et al. | |
| 5,009,653 A * | 4/1991 | Osborn, III | 604/387 X |
| 5,074,856 A | 12/1991 | Coe et al. | |
| 5,087,254 A * | 2/1992 | Davis et al. | 604/386 |
| 5,125,918 A | 6/1992 | Seidy | |
| 5,133,704 A * | 7/1992 | Wheeler | 604/387 |
| 5,133,705 A * | 7/1992 | Nakanishi et al. | 604/387 |
| 5,154,715 A * | 10/1992 | Van Iten | 604/387 |
| 5,176,671 A * | 1/1993 | Roessler et al. | 604/386 |
| 5,201,727 A | 4/1993 | Nakanishi et al. | 604/390 |
| 5,221,275 A | 6/1993 | Van Iten | 604/387 |
| 5,275,591 A | 1/1994 | Mavinkurve | 604/387 |
| 5,389,094 A * | 2/1995 | Lavash et al. | 604/386 |
| 5,391,162 A | 2/1995 | Widlund et al. | 604/385.2 |
| 5,489,283 A * | 2/1996 | Van Tilburg | 604/387 |
| 5,520,676 A * | 5/1996 | Lavash | 604/358 |
| 5,578,026 A * | 11/1996 | Lavash et al. | 604/386 |
| 5,620,430 A * | 4/1997 | Bamber | 604/386 |

FOREIGN PATENT DOCUMENTS

| | | |
|---|---|---|
| AU | A7415687 | 6/1987 |
| AU | B8188587 | 11/1987 |
| AU | A1208688 | 2/1988 |
| AU | A1906688 | 7/1988 |
| AU | A1972688 | 7/1988 |
| AU | A2001388 | 7/1988 |
| AU | A2157988 | 8/1988 |
| AU | A3224289 | 3/1989 |
| AU | A3276489 | 4/1989 |
| AU | A3600689 | 6/1989 |
| AU | A4114189 | 9/1989 |
| AU | A4170989 | 9/1989 |
| AU | A5146490 | 3/1990 |
| CA | 2023577 | 2/1992 |
| DE | 1491234 | 4/1969 |
| DE | 3319421 A1 | 11/1984 |
| EP | 0091412 B2 | 3/1983 |
| EP | 0130848 A2 | 7/1984 |
| EP | 0127103 A2 | 12/1984 |
| EP | 0155515 A1 | 9/1985 |
| EP | 0345703 A1 | 6/1988 |
| EP | 0280998 A1 | 9/1988 |
| EP | 0301491 A1 | 2/1989 |
| EP | 0301491 | 2/1989 |
| EP | 0304644 | 3/1989 |
| EP | 0334644 A2 | 3/1989 |
| EP | 0314535 A1 | 5/1989 |
| EP | 0409307 A2 | 7/1989 |
| EP | 0330206 | 8/1989 |
| EP | 0330206 A1 | 8/1989 |
| EP | 0331018 A1 | 9/1989 |
| EP | 0337438 A1 | 10/1989 |
| EP | 0337438 | 10/1989 |

| | | | |
|---|---|---|---|
| EP | 0347319 A1 | 12/1989 |
| EP | 0359501 A2 | 3/1990 |
| EP | 0360285 A2 | 3/1990 |
| EP | 0360680 A2 | 3/1990 |
| EP | 0426235 A2 | 5/1991 |
| FR | 2586558 | 3/1987 |
| GB | 2048684 A | 12/1980 |
| GB | 2161384 A | 1/1986 |
| GB | 2161384 | 1/1986 |
| JP | 4036391 | 12/1965 |
| JP | 4612554 | 5/1971 |
| JP | 4843500 | 9/1971 |
| JP | 4859395 | 11/1971 |
| JP | 4873497 | 12/1971 |
| JP | 4925294 | 6/1972 |
| JP | 4918398 | 5/1974 |
| JP | 5010718 | 4/1975 |
| JP | 50100399 | 8/1975 |
| JP | 50-44720 | 12/1975 |
| JP | 52117494 | 9/1977 |
| JP | 54154696 | 10/1979 |
| JP | 5516135 | 2/1980 |
| JP | 5720172 | 4/1982 |
| JP | 59225058 | 12/1984 |
| JP | 61154931 | 3/1985 |
| JP | 60158828 | 10/1985 |
| JP | 6151810 | 4/1986 |
| JP | 52-117394 | 9/1997 |
| WO | WO9207536 | 5/1992 |
| WO | PCT92/07536 | 5/1992 |
| WO | WO9207537 | 5/1992 |
| WO | PCT92/07537 | 5/1992 |
| WO | WO921/07537 | 5/1992 |

OTHER PUBLICATIONS

Exhibit 1: Oct. 1, 1998, Response to the Office Action communicating Notices of Opposition of McNeil–PPC, Inc.; SCA Mölnlycke AB; and Paul Hartmann AG, to the grant of European Patent 0,590,675 / 93 115,848.9.

Exhibit 2: Mar. 22, 1999, observations of the Opposition Division of the EPO regarding the Oppositions to the grant of European Patent 0,590,675 / 93 115,848.9.

Exhibit 3: Jan. 13, 1999, Resply to McNeil–PPC, Inc., to the Respone to the Office Action communicating Notices of Opposition of McNeil–PPC, Inc. and SCA Mölnlycke AB, to the grant of European Patent 0,590,047 / 93 115,757.2.

Exhibit 1: Jan. 15, 1999, Reply to SCA Mölnlycke AB, to the Response to the Office Action communicating Notices of Opposition of McNeil–PPC, Inc. and SCA Mölnlycke AB, to the grant of European Patent 0,590,047 / 93 115,757.2.

European Patent Office Decision on the Oppositions to European Patent No. EP–B–595047.

Exhibit 1: Notice of Opposition of McNeil–PPC, Inc., to the grant of European Patent 0,590,675/93115848.9.

Exhibit 2: Notice of Opposition of SCA Mölnlycke AB, to the grant of European Patent 0,590,675/93115848.9.

Exhibit 3: Notice of Opposition of Paul Hartmann AG, to the grant of European Patent 0,590,675/93115848.9.

Exhibit 4: Response filed Aug. 20, 1998, to the Office Action of Apr. 16, 1998, communicating Notices of Opposition of McNeil–PPC, Inc. and SCA Mölnlycke AB, to the grant of European Patent 0,595,047/93115757.2.

* cited by examiner

SANITARY NAPKIN WITH GARMENT ATTACHMENT PANELS

This application is a continuation of application Ser. No. 08/255,843 entitled "SANITARY NAPKIN WITH GARMENT ATTACHMENT PANELS" and filed in the U.S. Patent and Trademark Office on Jun. 8, 1994 now abandoned, which is a continuation of application Ser. No. 07/954,524 entitled "SANITARY NAPKIN WITH GARMENT ATTACHMENT PANELS" and filed in the U.S. Patent and Trademark Office on Sep. 30,1992, now abandoned. The entire contents of these applications are hereby incorporated by reference.

FIELD OF THE INVENTION

This invention relates to sanitary napkins and more particularly to a sanitary napkin with an elongated absorbent pad and a pair of garment attachment panels. The garment attachment panels control the lateral disposition of the edges of the crotch portion of an undergarment and the deflection or configuration assumed by the side edges of the absorbent pad.

BACKGROUND OF THE INVENTION

The basic form of sanitary napkins, upon which the present invention is an improvement, are well known. In a typical structure, an absorbent is enclosed between a bodyside liquid-permeable cover and a garment side liquid-impermeable baffle. The cover and baffle may extend beyond the absorbent and be bonded together to form a "side edge" or peripheral seal. In use, the sanitary napkin is mounted on the crotch portion of an undergarment such as a panty and, for convenience in description, the working environment of the invention will be assumed to be in a panty as worn by a female. However, the inventive concept may also be applied to infant care, child care, and adult care incontinent garments.

Another form of conventional sanitary napkin, a flat pad with garment attachment panels (wings or flaps), potentially offers some functional improvements and advantages over a plain pad. Typically, the form of this product before use is a flat pad with a pair of opposite garment attachment panels extending laterally outward from an absorbent. The garment attachment panels are often an extension of the conventional cover and baffle between which the absorbent is sandwiched. In use, the absorbent element overlays the crotch portion of the panty in the normal way and the garment attachment panels are folded under to encircle the crotch portion. The garment attachment panels may be secured beneath, to each other, and/or to the panty crotch portion, by suitable adhesive or mechanical fasteners. In use, the relative lateral disposition of the point at which each of the panels are folded (line of fold) is determined substantially by the user, in somewhat random fashion. Between users, or successive applications by a single user, there may be substantial variation in "fit" and working configuration with respect to the spacing of the fold in the panel from the edge of the absorbent and with respect to the disposition of the panty elastic relative to the edge of the absorbent (and to the fold). Performance of the napkin may vary accordingly.

The garment attachment panels on flat conventional pads typically are designed to wrap around or fold over the panty elastic and form an upward element that fits into the groin of the wearer. Typically, the garment attachment panels are nonabsorbent or minimally absorbent and so this arrangement places additional nonabsorbent material in the crotch region and, during use, the added material has a tendency to fold over onto the absorbent element. For the comfort and protection of an appropriate fit in the groin, the user is dependent upon appropriate disposition and behavior of the panty elastic.

Van Tilburg (U.S. Pat. Nos. 4,589,876 and 4,687,478) and Mattingly (U.S. Pat. No. 4,608,047) disclose variations on and potential improvements over the general form of a flat pad with garment attachment panels referred to above.

The teachings in the two Van Tilburg patents are substantially similar. They show a flat pad with laterally extending panels which fold over the panty elastic (crotch portion edge) but do not encircle the crotch portion. Each panel has two substantially parallel "lines of juncture" which provide "axes of flexibility" to help determine where the panel folds—upward in relation to the absorbent edge and downward over the elastic edge of the panty. In use, it is intended that the panty elastic is pulled up into the groin so that the panel, enfolded about it, lies against the laterally outward facing surfaces of the labia majora, forming a dam against lateral flow of fluid. However, the desired configuration is not easily obtained in practice. Because the panty elastic is allowed to go up into the groin, the garment attachment panels must be of sufficient length to cover the panty elastic throughout the length of the labia majora. Making the garment attachment panels long can create a problem in that the end portions of the garment attachment panels (toward the front and back of the pad) which have been folded around the panty crotch are "fighting" with the panty elastic which is flaring out and cupping to the body. This can result in discomfort for the user and can cause the panels to come loose from the panty during wear. When the panels come loose the panty elastic will tend to push the panels up onto the absorbent.

The teaching of Mattingly is essentially that described above for a conventional flat pad with garment attachment panels but the disclosure is directed particularly to the "drapability" or sufficient flexibility of the panels. The panels may be folded at any lateral point to match the width of the panty crotch portion and avoid wrinkling. The panels may be of sufficient length to encircle the crotch portion and adhere to each other or to the panty. Mattingly recognizes the problem of the tendency of the panty crotch edge "to enfold onto the body facing surface of the napkin" but he suggests allowing the folded panel configuration to be determined by panty crotch width rather than providing positive control of the juxtaposition of the panty elastic with the edge of the absorbent element.

The teachings in McCoy (U.S. Pat. No. 4,900,320), Salerno (U.S. Pat. No. 4,940,462) and Seidy (U.S. Pat. No. 5,125,918) depart substantially from the form of conventional flat pads with garment attachment panels described above. In that form and before use, the panels are essentially lateral extensions of the cover and/or baffle surfaces of the pad. But in McCoy, separate panels are affixed beneath the absorbent, each at a point inward from the longitudinal edge of the absorbent. This enables the panels to be folded around the crotch portion of the panty, gathering the crotch portion under the absorbent and removing its edges from proximity with the edges of the absorbent and the possibility of becoming wet or stained. But attachment of the panels inward of the absorbent risks gathering the panty crotch so much that the user feels some discomfort. The thinner the pad and the wider the panty crotch, the more likely this is to occur. If the absorbent is made wider to avoid this problem, users with narrow crotch widths will experience some discomfort.

In Salerno, the garment attachment panels, which may comprise extensions of the cover or baffle portions of the sanitary napkin, are longitudinally expandable. Such panels, folded over a side of the crotch portion of an undergarment, may more readily conform to the contour of the undergarment and "provide lateral protection without bunching of the undergarment". But Salerno does not suggest use of the garment attachment panels to control lateral disposition of the undergarment crotch portion edge and, particularly, not of an elasticized edge in relation to an absorbent element in such a way as to prevent the elasticized edge from pulling in on top of the absorbent. Salerno's design does not particularly limit the disposition of the garment attachment panels when secured. They do not overlap and fasten together to establish a predetermined configuration when in use.

In Seidy, the "garment attachment panels" are truncated and supported at the opposite lateral edges of the absorbent, extending inwardly and somewhat stiffly in a "prefolded flexible position". This enables the panty crotch portion to be maneuvered into position under the absorbent and retained by the panels without the need for additional attachment adhesive.

As with Mattingly, the McCoy, Salerno and Seidy patents are primarily concerned with various aspects of treatment of the panty crotch portion in relation to the sanitary napkin. Mattingly teaches the avoidance of wrinkling; McCoy teaches a particular approach to shielding the crotch portion from wetting and staining; Salerno teaches "side-protection along the entire longitudinal edges of the napkin" without bunching of the undergarment; and Seidy teaches the provision of panty edge shielding flaps without requiring "additional attachment adhesive."

None of these references suggest making use of garment attachment panels to enhance directly the performance of the sanitary napkin as a whole.

SUMMARY OF THE INVENTION

Accordingly it is a general object of the invention to provide a sanitary napkin with garment attachment panels which perform their intended function of protecting the undergarment crotch portion and anchoring the sanitary napkin to it while permitting the absorbent portion of the napkin to conform to the body of the user.

This object may be achieved in a sanitary napkin which includes an elongated absorbent pad having opposite longitudinal side edges which are deflectable with respect to a central portion of the pad. The pad includes an absorbent contained between a liquid-permeable cover and a liquid-impermeable baffle. The pad includes a control mechanism carried by the pad, adjacent the side edges, for selectively controlling the deflection of the side edges so as to optimize the function of the sanitary napkin.

The control mechanism may comprise at least one garment attachment panel, normally extending generally downward and inward from its attachment at or adjacent to one of the deflectable side edges. In use, the garment attachment panel is anchorable under the crotch portion of an undergarment so as to confine the crotch portion and substantially define its lateral disposition relative to the pad, and particularly to the absorbent portion of the pad.

The garment attachment panel may include a fixed portion attached to the underside of the pad and a free portion extending as a continuation of the fixed portion and diverging from the underside of the pad. In use, the lateral disposition of the fixed portion of the panel with respect to the pad may define an outer lateral limit of disposition for a side edge of the crotch portion of an undergarment.

An anchoring mechanism for securing the garment attachment panels beneath the undergarment crotch portion may provide only a limited range of adjustment so as to facilitate accurate mounting of the sanitary napkin on the undergarment.

Another object of the invention is to provide a sanitary napkin with a mechanism for positively controlling the disposition of the side edges of the crotch portion of an undergarment and particularly an elasticized edge (panty elastic). A more specific object of the invention is to provide a sanitary napkin with a control mechanism for pulling the panty elastic and holding it under the absorbent or at least no higher than closely alongside a lateral edge of the absorbent.

A further object of the invention is to provide a sanitary napkin with garment attachment panels which, in use, exert a pull on the side edges of the pad thus overcoming any tendency for the side edges to fold in over the absorbent.

Still another object of the invention is to provide a sanitary napkin in which the control exercised on the side edges by a pair of garment attachment panels helps to bias the pad convexly upwards, conforming more closely to the body and bringing it closer to the source of menstrual flow.

Yet another object of the invention is to provide a sanitary napkin having a control mechanism which prevents the elasticized edge of an undergarment crotch portion from folding up and over the absorbent.

Yet another object of the invention is to provide a sanitary napkin in which the absorbent is free to conform to the body. A further specific object is to provide a sanitary napkin which controls panty elastic disposition so that bias of the panty elastic may assist in conforming the absorbent to the body.

Other objects and advantages of the present invention will become more apparent to those skilled in the art in view of the following description and the accompanying drawings.

DETAILED DESCRIPTION OF THE PREFERRED EMBODIMENTS

Referring to FIGS. 1, 2, 3 and 5, a sanitary napkin 10 is shown which represents an exemplary embodiment of the invention. It comprises an elongated absorbent pad 12 and a pair of garment attachment panels 14 and 16. Panels 14 and 16 may be referred to as a first garment attachment panel and a second garment attachment panel, respectively.

The form and construction of the absorbent pad 12 is generally conventional and it will be described only briefly. An absorbent 18 is enclosed between a liquid-permeable cover 20 and a liquid-impermeable baffle 22. The baffle 22 carries a longitudinally central strip of garment adhesive 24, covered before use by a conventional peel strip or release paper 26.

The cover 20 and the baffle 22 extend beyond the absorbent 18 and are bonded together to form an edge or peripheral seal 28 extending from a seal line 30, closely bordering the absorbent 18, to an outer peripheral edge 32. Along the opposite longitudinal sides of the absorbent pad 12, the edge seal 28 defines opposite longitudinal side edges 34 and 36 of the absorbent pad 12, extending laterally from closely adjacent opposite longitudinal side edges 38 and 40 of the absorbent 18. Side edges 34 and 36 may be referred to as a first side edge and a second side edge of the absorbent pad, respectively. The side edges 34 and 36 have upper and lower walls 42, 44 and 46, 48 respectively, formed by the respective extensions of the cover 20 and the baffle 22.

Figure 1:
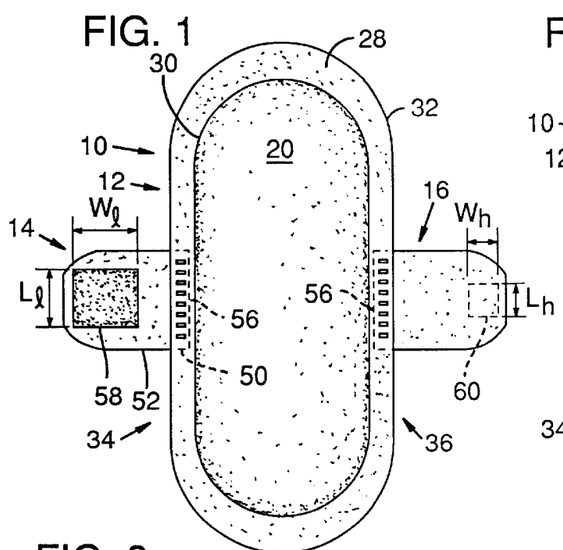
FIG. 1 is a top or bodyside view of a sanitary napkin according to the invention with its garment attachment panels spread open as they may be before installation.
Figure 2:
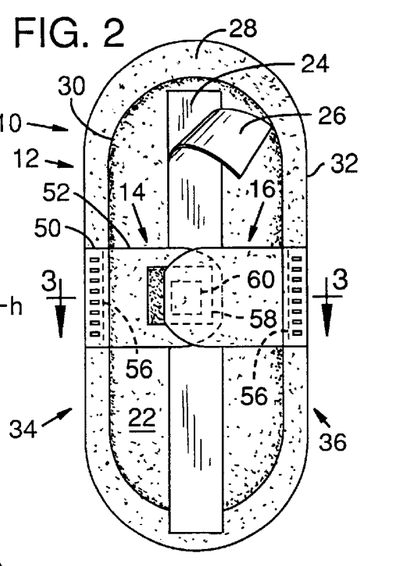
FIG. 2 is a bottom or garment side view of the sanitary napkin with the garment attachment panels closed.
Figures 3, 4, 5:
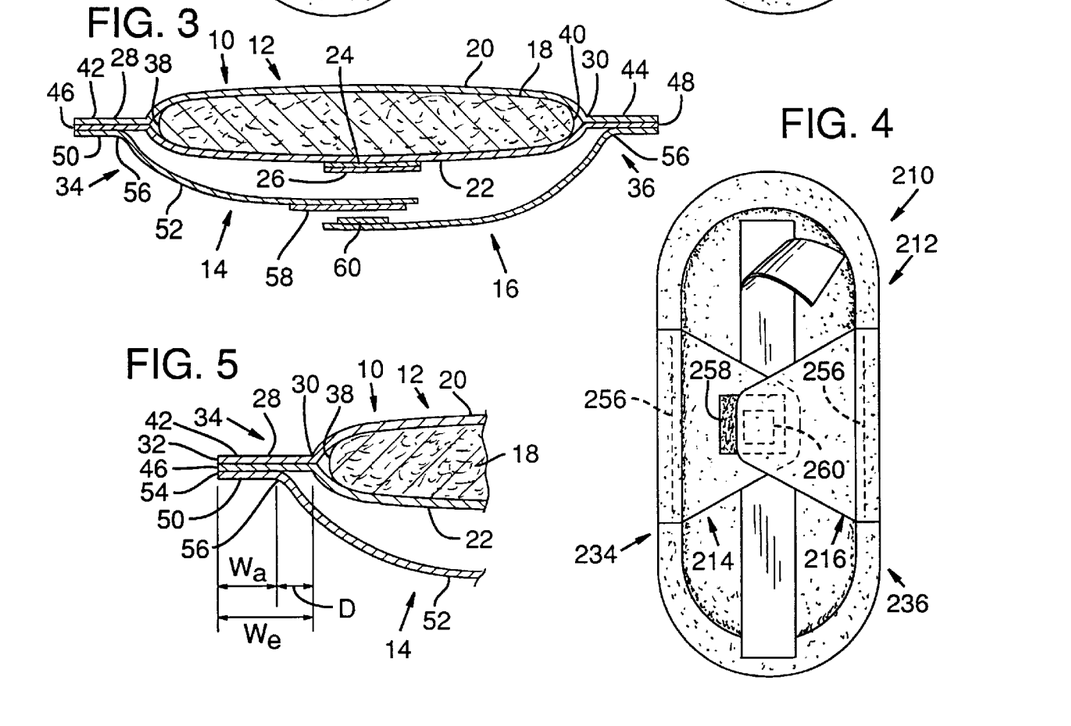
FIG. 3 is a cross-sectional view of FIG. 2 taken on line 3—3.
FIG. 4 is a view similar to FIG. 2 of an alternative embodiment of the invention.
FIG. 5 is a partial, enlarged cross-sectional view of the sanitary napkin shown in FIGS. 1–3 showing the attached relationship of a garment attachment panel to the edge seal.

Referring to FIG. 5, the garment attachment panels 14 and 16 are identical apart from the anchoring elements they carry and, therefore, only one will be described. The garment attachment panel 14 consists of a generally rectangular sheet of material which, in assembly, has a fixed or attachment portion 50 and, extending from it, a free portion 52. The attachment portion 50 overlays and is bonded to the lower wall 46 of the side edge 34. The attachment area extends from an outer edge 54 adjacent to the peripheral edge 32, to an inner edge or effective point of attachment 56. The effective point of attachment is equivalent to the lateral limit of the garment attachment panel. The free portion 52 of the garment attachment panel 14 diverges from or hinges at the effective point of attachment 56 and normally extends generally downward and inward.

The anchoring elements of the garment attachment panels 14 and 16, referred to above, comprise a mechanical fastener of conventional hook and loop type fabric—a relatively small patch 58 of loop material on the garment attachment panel 14 and a smaller patch 60 of hook material on panel 16. The fastener elements 58 and 60 are located so that the panels 14 and 16 may be anchored together under the absorbent 18 as shown, for example, in FIG. 12.

The invention may be practiced successfully with absorbent pads of a wide range of sizes and proportions as indicated in the following exemplary Table 1.

TABLE 1

| Dimensions (inches): | | Nominal | Range | Preferred Range |
|---|---|---|---|---|
| Pad 12: | Length | 9.0 | 7.0–13.0 | 8.0–11.0 |
| | Width | 3.5 | 2.0–4.5 | 2.5–4.0 |
| Panel 14, 16: | | | | |
| | Length | 2.0 | 1.0–5.0 | 1.5–3.0 |
| | Width | 2.25 | 1.5–2.75 | 1.75–2.5 |
| Attachment Width (Wa) | | 0.25 | 0.125–0.5 | 0.125–0.5 |

Exemplary ranges of size (dimensions in inches) for the loop and hook fastener elements 58 and 60 are as indicated in the following Table 2.

TABLE 2

| | Range | Preferred Range |
|---|---|---|
| Hook Element 60 - Width Wh | 0.25–1.0 | 0.25–0.5 |
| Loop Element 58 - Width Wl | 0.25–1.5 | 0.5–1.0 |
| Hook Element 60 - Length Lh | 0.25–3.0 | 0.25–1.5 |
| Loop Element 58 - Length Ll | 0.25–3.0 | 0.5–1.5 |

The scope of the invention also permits the use of a variety of materials, as well as variations in configuration. Other pad outline shapes are possible, such as barrel, rectangular or hourglass. In alternative designs, absorbent material could extend into the side edges 34 and 36.

Suitable materials for the garment attachment panels 14 and 16 include polymeric foams, nonwovens, elastomerics, or composites of these materials.

With regard to the anchoring means 58 and 60 for the garment attachment panels 14 and 16, alternative mechanical fasteners are possible. Adhesive fastening may also be used but the potential precision of a mechanical fastener is preferred as will be discussed further below.

Referring to FIG. 4, a second embodiment of the invention is shown. Here, a sanitary napkin 210 is shown having an absorbent pad 212 with a second exemplary size and shape of garment attachment panels 214 and 216. The panels 214 and 216 are carried by the longitudinal side edges 234 and 236 of absorbent pad 212. In this example, the garment attachment panels 214 and 216 are longer at their effective attachment points 256.

There are many suitable alternative arrangements for making the juncture between the absorbent pad and the garment attachment panel. Preferably, any arrangement should provide an "effective attachment point" on the underside of a side edge 34, 36 and 234, 236 respectively, and inset from its outer periphery, as exemplified at 256 and 56, see FIGS. 4 and 5, respectively. The garment attachment panel may, for example, be formed from an extension of the cover and/or the baffle of the absorbent pad. It may be a separate piece of material, wrapping over the side edges 34 and 36 with the free portion of panel diverging from the underside of the side edge. The fixed portion 50 of the garment attachment panel may be bonded between the layered components of the side edge, the material of the panel emerging to fold downward and inward under the pad, to function as the garment attachment panel.

Figure 11:
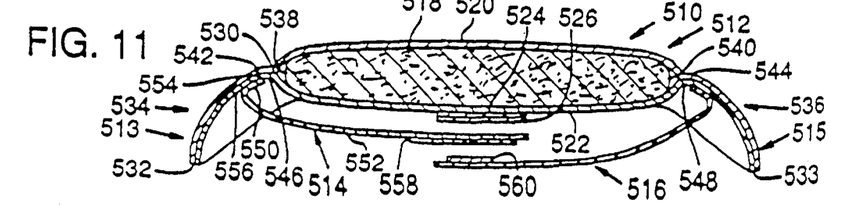
FIG. 11 is a cross-sectional view of the fifth embodiment, similar to a view taken on line 11—11 of FIG. 10 but with the garment attachment panels closed.

Another mode of attachment of a garment attachment panel is shown in FIG. 11. Here, compared with the first embodiment shown in FIG. 5, the attachment configuration for a garment attachment panel has been reversed. The fixed portion of the panel has been laid on the underside of a "side edge" with the panels initially directed outward. This embodiment will be discussed in more detail below.

Figure 6:
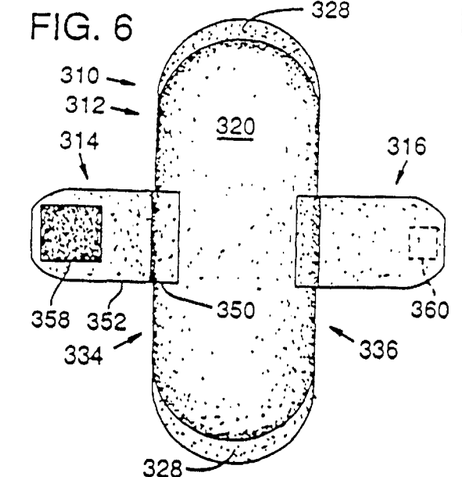
FIGS. 6 and 7 are views similar to FIGS. 1 and 2 of a third embodiment of a sanitary napkin of the invention.
Figure 7:
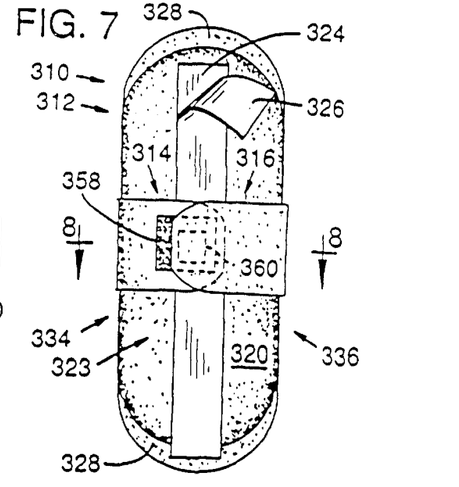
Figures 8, 9, 10:
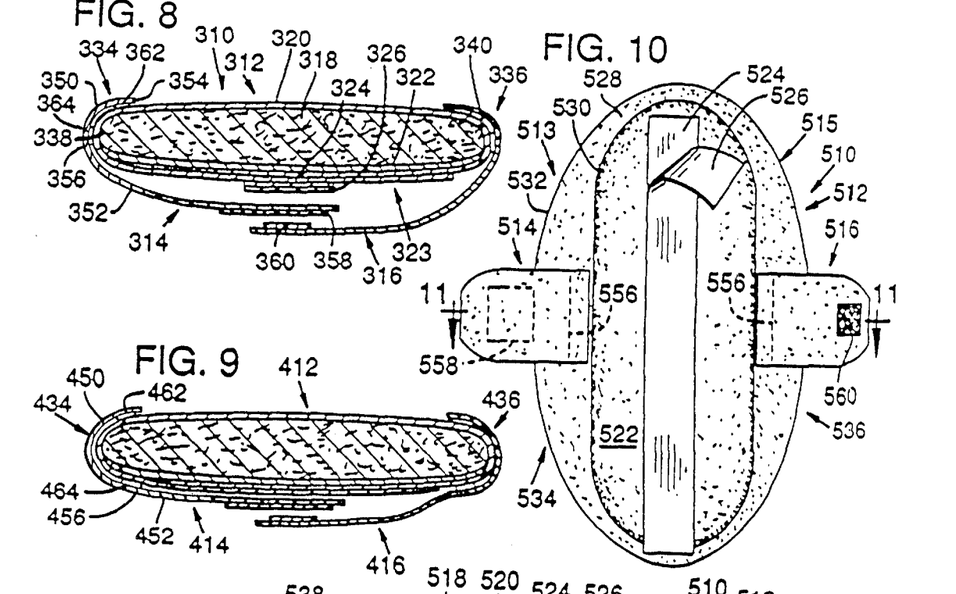
FIG. 8 is a cross-sectional view of the third embodiment of the invention taken on line 8—8 of FIG. 7.
FIG. 9 is a view similar to FIG. 8 of a fourth embodiment of the invention.
FIG. 10 is a bottom or garment side view of a fifth embodiment of the invention.

Referring to FIGS. 6, 7 and 8, a third embodiment of the invention is shown. Here, a sanitary napkin 310 is depicted having a generally conventional elongated absorbent pad 312 and a pair of garment attachment panels 314 and 316. An absorbent 318 is contained between a liquid-permeable cover 320 and a liquid-impermeable baffle 322. The cover 320 completely wraps the absorbent, overlapping on the garment side 323 of the pad and thus overlaying the baffle 322. A strip of garment adhesive 324 which is protected by a peel strip 326 are provided on the garment side 323 of the pad. The cover 320 is sealed at each of its opposite ends by an end seal 328.

In this third embodiment, the garment attachment panels 314 and 316 may be similar in construction and range of size and shape to those suggested above for the garment attachment panels 14 and 16. The mechanical fastener provided for the garment attachment panels 314 and 316 may also be similar in all respects to that of the first embodiment and is represented by the hook and loop type fastener elements. The fastener includes a loop patch 358 and hook patch 360 carried by the panels 314 and 316, respectively. The mounting of the garment attachment panels 314 and 316 on the longitudinally central portions of the opposite side edges 334 and 336 of the pad 312 is similar and, therefore, only one will be described. As is conventional, the pad 312 has a generally smooth outer surface and the side edges 334 and 336 are well rounded. A fixed portion 350 of the panel 314 wraps an upper portion of the side edge 334 extending from a fixed portion outer edge 354 to an effective point of attachment 356. The effective point of attachment 356 is at the side of the rounded side edge 334 so that a free portion 352 of the garment attachment panel, before use, may extend generally tangentially downward from the side edge. The garment attachment panel 314 may be secured to the side edge 334 by any suitable means such as the spaced apart strips of construction adhesive 362 and 364 shown in FIG. 8.

Still referring to FIGS. 6, 7 and 8, satisfactory performance of the wrapped pad 312 is obtained with some variation of the degree of wrap of the fixed portions 350, of the garment attachment panels 314 and 316, about the rounded side edge 334.

Referring to FIG. 9, an absorbent pad 412 is shown having a pair of garment attachment panels 414 and 416 carried by the opposite longitudinal rounded side edges 434 and 436 of the pad 412. The attachment of the garment attachment panel 414 is typical and includes a fixed or attached portion 450 and a free portion 452. The free portion 452 diverges from the pad 414 at an effective attachment point 456. The limits of the fixed portion 450 are defined substantially by spaced apart upper and lower construction adhesive strips 462 and 464. Taken together, the embodiments shown in FIGS. 8 and 9 represent a preferred range of disposition of an effective attachment point for a garment attachment panel on a wrapped pad. This range varies from being aligned approximately horizontal alongside the rounded edge, as at 356 in FIG. 8, to a disposition at a lower portion of the rounded edge, as at 456 in FIG. 9.

Referring to FIGS. 10 and 11, a fifth embodiment of a sanitary napkin 510 is shown. This is in effect a sanitary napkin with "double panels". The sanitary napkin 510 includes an elongated absorbent pad 512 and a pair of garment attachment panels 514 and 516. The pad 512 is in most respects conventional. An absorbent 518 is contained between a liquid-permeable cover 520 and a liquid-impermeable baffle 522. A garment adhesive strip 524 is protected by a conventional peel strip 526. Lateral extensions of the cover 520 and the baffle 522 are bonded together to form an edge seal 528. The edge seal 528 extends from a seal line 530 surrounding the absorbent 518. Unconventionally, the longitudinal side portions of the edge seal 528 are broadened to define opposite longitudinal side edges 534 and 536 of the pad 512 and to give the pad 512 an oval or diamond shaped ("Stealth") appearance, see FIG. 10.

Major longitudinal central portions of the extended side edges 534 and 536 define opposite outer garment attachment panels 513 and 515. These panels have upper and lower walls 542, 544 and 546, 548 respectively, and are bounded outwardly by opposite peripheral edges 532 and 533 and inwardly, approximately, by the opposite lateral side edges 538 and 540 of the absorbent 518. The inner or main garment attachment panels 514 and 516 may be similar in all respects to those described above, for example, in connection with the first embodiment. As a mechanical fastener, they carry relatively small patches of hook and loop type fastener; in particular a loop portion 558 and a hook portion 560. The panels 514 and 516 are similar and, therefore, only the attachment arrangement of the garment attachment panel 514 will be described. A fixed or attachment portion 550 of the panel is bonded to the lower or inner wall 546 of the outer panel 513. It extends from an inner edge 554 to an effective attachment point 556, from which a free portion 552 of the garment attachment panel diverges to extend, during use, inwardly and somewhat downwardly.

The embodiment of the invention represented by FIGS. 10 and 11 may be used successfully with a wide range of dimensions, as indicated by the examples given in Table 3.

TABLE 3

| Dimensions (inches) | Nominal | Range | Preferred Range |
| --- | --- | --- | --- |
| Pad 512 - length | 9.0 | 7.0–13.0 | 8.0–11.0 |
| Absorbent 518 - width | 3.0 | 2.0–4.5 | 2.5–4.0 |
| Outer panel 513, 515 | | | |
| length | 5.0 | 3.0–7.0 | 4.0–6.0 |
| width | 1.25 | 0.75–1.75 | 0.75–1.5 |
| Garment Attachment Panel 514, 516 | | | |
| length | 2.0 | 1.0–5.0 | 1.5–3.0 |
| width | 2.0 | 1.5–2.75 | 1.75–2.5 |
| attachment width | 0.25 | 0.125–0.5 | 0.125–0.5 |

The modes of using and performance characteristics of all embodiments of the invention disclosed herein are similar and will be described first with reference to the first embodiment, the sanitary napkin 10 shown in FIGS. 1, 2, 3, 5 and 12.

In preparation for use, the peel strip 26 is removed from the absorbent pad 12 exposing the garment adhesive 24. With the garment attachment panels 14 and 16 in an open position, the absorbent pad 12 is centered and mounted on the crotch portion 130 of an undergarment in the usual way. Next, after ensuring that the panty crotch portion 130 is uniformly distributed over the underside of the baffle 22, the garment attachment panels 14 and 16 are closed by bringing together the hook and loop fastener elements 58 and 60. As seen in the drawings, these fastener elements are relatively small. In fastening the panels 14 and 16, the degree of overlap of the fastener elements 58 and 60 may vary somewhat, providing some adjustability or variation in the tightness or snugness with which the panels 14 and 16 are fastened and a user may choose to make some individual use of this factor. However, the range of adjustment is intentionally limited. The range provided in a given pad is large enough to make it easy for the user to install the product, but small enough to ensure that it is always installed so that it will function as intended. Some preferred ranges of adjustment are indicated in Table 2 for the fastener elements 58 and 60.

Figure 12:
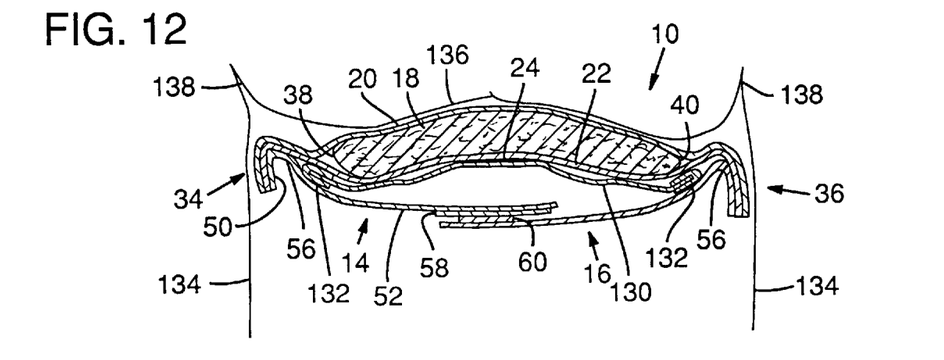
FIG. 12 is a cross-sectional view of a typical in-use configuration of the sanitary napkin shown in FIGS. 1–3.

The range of lateral adjustment is determined by the corresponding width dimensions (Wl) of the loop element 58 and width dimension (Wh) of the hook element 60. Normally, the garment attachment panels 14 and 16 are fastened so that the fastener elements 58 and 60 are approximately centered, one on the other, as indicated in FIG. 12. The configuration of the sanitary napkin of the invention, including the range of adjustment provided for the fasteners 58 and 60, is such that when the garment attachment panels 14 and 16 are properly fastened, the panty crotch portion 130 is always confined beneath the pad. This means that the crotch portion edge and the panty leg elastic 132 are disposed laterally substantially no further out than the edges 38 and 40 of the absorbent 18. Alternatively, the crotch portion 130 should be no higher than alongside its lateral sides.

The limit of the lateral disposition of the panty elastic 132 is determined by the "stop" provided at the effective attachment point 56 of the respective garment attachment panels 14 and 16. The chosen location for the effective attachment point 56 is important to the function of the sanitary napkin. If it is too far in on the side edges 34 and 36, and hence too close to the longitudinal side edges 38 and 40 and to the seal line 30, the pull or tension set up in the garment attachment panels 14 and 16 when they are fastened will have relatively little effect in controlling deflection of the side edges 34 and 36. If the effective attachment point 56 is too far out on the side edges 34 and 36, the pull of the garment attachment panels 14 and 16, when fastened, may cause an undesirable extreme downward distortion of the side edges.

Referring to FIG. 5, when the effective width (We) of the side edges 34 and 36 is in the range from about 0.25 to about 1.0 inches, a preferred range of width (Wa) for the fixed attachment portion 50 of the panel is from about 0.125 to about 0.5 inches. A preferred spacing (D) between the effective point of attachment 56 and the absorbent side edges 38 and 40 is in the range of about one third to three quarters of the width (We) of the side edges 34 and 36.

When the panty leg elastic 132 is shielded by controlling its position rather than by simply covering it with a simple long garment attachment panel, as is taught in Van Tilburg, a shorter garment attachment panel may be used effectively. See the preferred range of panel lengths of about 1.5 to about 3.0 inches shown in Table 1 above. With shorter panels, the possible discomfort of longer panels and inconvenience of their "popping open" is avoided.

Referring to FIG. 12, the sanitary napkin 10 is mounted on the crotch portion 130 of the undergarment. Before the undergarment is pulled up, the garment attachment panels 14 and 16 are fastened with the fastener elements 58 and 60 approximately centered, one on the other, and the side edges 34 and 36 of the pad are thus pulled down slightly and the absorbent 18 arches convexly upwards. FIG. 12 shows how a sanitary napkin so adjusted may appear during use. The side edges 34 and 36 are folded downward and "gasket" comfortably against the thighs 134. The upwardly convex form of the absorbent 18 fits more closely to the source of the menstrual flow and more comfortably against the labia 136.

Important aspects of the invention are control of the deflection of the side edges, such as the side edges 34 and 36, of the absorbent pad and control of the edges 132 of the crotch portion 130 of an undergarment.

As discussed above, fastening the garment attachment panels 14 and 16 helps configure the absorbent pad 12 for effective use. In addition, when they are properly fastened, the downward pull of the garment attachment panels 14 and 16 on the side edges of the absorbent pad 12 prevent the edges of the pad 12 from collapsing against or folding in on top of the absorbent during preparation for, or during use.

Figure 13:
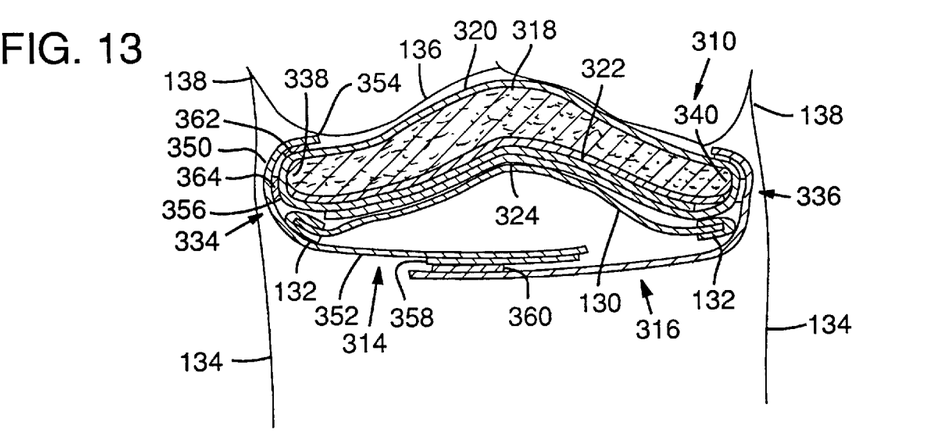
FIGS. 13 and 14 are cross-sectional views of typical in-use configurations of the sanitary napkin shown in FIGS. 6, 7 and 8.
Figure 14:
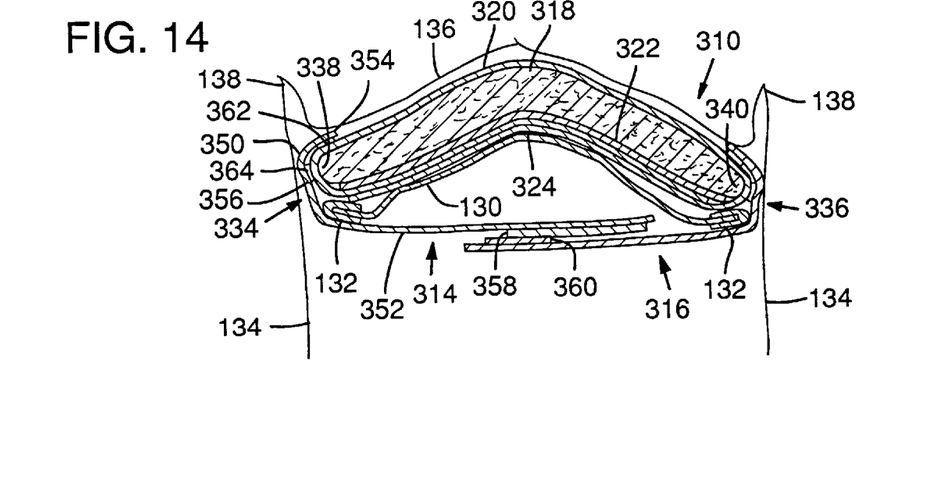

The key to the control of the edges of the crotch portion 130 of the undergarment, particularly when the edges are elasticized, is the disposition, during use, of the effective attachment point 56 of the garment attachment panel. The disposition of this attachment point 56 establishes a limit or stop for lateral disposition of the panty elastic 132. Preferably, and as shown in FIGS. 12, 13 and 14, the panty elastic is confined to being under the absorbent side edges 38 and 40, or no higher than alongside the absorbent side edge. This control prevents the panty elastic from pulling in onto the top of the absorbent. Another positive result of the panty elastic disposition control is that with the elastic held under the absorbent side edges, the panty elastic may help to bias the absorbent upwards for a better fit to the body.

Another advantage of the invention is that the configuration of the sanitary napkin, and particularly that of the fastened garment attachment panels 14 and 16, is such that, in preparation for use, a user cannot inadvertently fold and fasten the garment attachment panels 14 and 16 over the panty elastic 132 in such a way as to allow the panty elastic to pull the panel itself up into the groin.

Turning now to FIGS. 6, 7, 8, 13 and 14, a third embodiment of the invention is shown wherein the garment attachment panels 314 and 316 force or hold the panty elastic 132 under the absorbent 318. Particularly in this case, the sides of the absorbent 338 and 340 are allowed to fold and fit into the groin and thighs of the wearer. The garment attachment panels 314 and 316 also protect the panty elastic from side stain or smear by preventing the elastic from overlapping the side edges 338 and 340 of the absorbent core. The pull of the garment attachment panels may also buckle the absorbent into a convex shape for better fit to the body.

FIGS. 13 and 14 are cross-sectional views of two typical configurations of sanitary napkins according to the third embodiment during use. In FIG. 14, the garment attachment panels 314 and 316 are fastened together somewhat more tightly than in FIG. 13, resulting in a greater upward convexity of the absorbent 318. Note the difference in overlap of the panels 314 and 316 and the fastener elements 358 and 360 in the two drawings. In the resulting configuration of FIG. 13, the edges 338 and 340 of the absorbent are raised and folded somewhat to fit into the groin 138 of the wearer without any interference from the panty elastic or the garment attachment panel. The panty leg elastic 132 is protected under the absorbent and helps to force the absorbent edge into the groin. The disposition of the effective attachment point 356 prevents the panty leg elastic from going up into the groin.

In FIG. 14, the relatively tighter fastening of the garment attachment panels 314 and 316 tends to pull the side edges 338 and 340 of the absorbent somewhat downward, arching the absorbent, and allowing the absorbent edges to fit closely to the thighs. The panty leg elastic 132, held under the absorbent by the garment attachment panels, assists in biasing the center of the absorbent into an arch that fits into the labia.

Referring now to FIGS. 10 and 11, a "double panel" embodiment is shown. This embodiment is not shown in use, but the basic configuration of this embodiment apart from the addition of the outer panels 513 and 515, is very similar to that of the first embodiment, see FIG. 3. In use, the basic function of the garment attachment panels 514 and 516 is similar to that of the first embodiment but the addition of the outer panels 513 and 515 provides some modification of the performance.

In use, the garment attachment panels 514 and 516 pull the outer panels 513 and 515 down against the edge of the panty elastic 132 and the user's thighs 134 allowing these panels to protect the panty from side staining or smearing. The garment attachment panels 514 and 516 also assist with protection, fit, and comfort by forcing the panty elastic 132 under the absorbent 518 and preventing the panty elastic from pushing the outer panels or the elastic itself onto the top of the absorbent. Collectively, the panels also enhance fit and protection by reducing pad bunching during wear. Additional material may be incorporated into the outer panels 513 and 515 for absorbency. However, the panels are designed to be soft and conformable for optimum fit to the body and for comfort. The garment attachment panels 514 and 516 may be made from a variety of materials but are preferably stiffer than the outer panels, to assist in their function of holding the panty elastic under the pad. The stiffness and outwardly directed attachment of the garment attachment panels 514 and 516 makes it less likely that they will be caught on the garment adhesive 524 during installation.

Another feature of sanitary napkins of the fifth embodiment is that, given the extra protection afforded by the outer panels 513 and 515, the garment attachment panels 514 and 516 may be sized so that they do not bunch the distal portions of the panty crotch elastic, thereby enhancing comfort. The garment attachment panels 514 and 516 also reduce pad bunching by helping to maintain the width of the pad and preventing its sides from collapsing in towards the center. While the garment attachment panels hold the center portions of the panty crotch under the pad, the longer outer panels 513 and 515 provide additional coverage of the distal portions of the panty elastic. The outer panels 513 and 515 are preferably soft and flexible and do not fasten to each other or to the undergarment so that they are free to comfortably gasket against the thighs for improved protection.

Referring to FIG. 11, the outwardly directed attachment of the garment attachment panel 514 may be moved or extended so that the effective attachment point is further out on the outer panel 513. Such an arrangement would exercise more direct control of a longitudinally central portion of the outer panel 513. The garment attachment panels 514 and 516 would still maintain the function of controlling panty elastic disposition under the absorbent as long as the garment attachment panels 514 and 516 and their fastener arrangement were sized appropriately, as described above.

We claim:

1. A sanitary napkin for mounting onto the bodyside of a crotch portion of an undergarment, and, during use, absorbing bodily excretions, comprising:

an elongated absorbent pad having a longitudinal axis, a longitudinally central portion and opposite longitudinal side edges, said side edges being deflectable with respect to said central portion, and including an absorbent contained between a bodyside, liquid-permeable cover and a garment side, liquid-impermeable baffle; and control means for selectively controlling deflection of said side edges during use, said control means being anchorable under said crotch portion of said undergarment, said anchoring establishing a generally downward pull on said side edge and preventing said side edge from folding in toward said absorbent, wherein said control means comprises first and second opposite garment attachment panels, normally extending generally downward and inward from said absorbent pad adjacent to said side edges and wherein said garment attachment panels include a fixed portion attached to the underside of said absorbent pad toward said side edge and a free portion diverging from the underside of said absorbent pad for, during use, extending under said crotch portion of said undergarment, wherein a garment attachment point is defined where said fixed and said free portions meet each other;

and including means for anchoring said free portions of said garment attachment panels so as to establish a predetermined deflection of said absorbent side edges and to facilitate accurate mounting of said sanitary napkin on said undergarment, and wherein said means for anchoring said free portions of said garment attachment panels comprises mating fastener elements, one on each of said garment attachment panels, said fastener elements being configured as to provide substantially only a single predetermined lateral relations of one garment attachment panel to the other.

2. The sanitary napkin of claim 1, wherein the predetermined deflection of said side edges and the predetermined particular confinement of said side edges of said crotch portion of said undergarment biases said absorbent pad into an upwardly convex form, closely fitting the body.

3. The sanitary napkin of claim 1, wherein said absorbent is longitudinally extending and has opposite longitudinal side edges and the deflectable side edges of the absorbent pad normally extend generally laterally with respect to said absorbent and, during use, the anchoring of said garment attachment panel configures said sanitary napkin so that each side edge of said crotch portion of said undergarment is supported approximately no higher than a side edge of said absorbent.

4. The sanitary napkin of claim 1, wherein the lateral disposition of said fixed portion of said garment attachment panel and the anchoring of said garment attachment panel configure said sanitary napkin so that each side edge of said crotch portion of said undergarment is supported approximately beneath a side edge of said absorbent and said absorbent is free to conform to the body of the user.

5. The sanitary napkin of claim 1, wherein said fixed portions of said garment attachment panels are disposed so that each side of said crotch portion of said undergarment is restrained adjacent to a side edge of said absorbent pad and prevented from overlaying said absorbent pad.

6. The sanitary napkin of claim 1, wherein said side edges of said absorbent pad have a lateral periphery and said absorbent has a longitudinally extending lateral side contiguous with said side edge and said attachment of said garment attachment panels has an inner lateral limit from which said free portion of said garment attachment panel diverges and said inner lateral limit is disposed between said lateral side of said absorbent and said lateral periphery of said side edge of said absorbent pad.

7. The sanitary napkin of claim 1, wherein said cover and said baffle extend laterally beyond said absorbent to define said side edges and wherein said garment attachment panels are secured to said baffle outwardly of said absorbent.

8. The sanitary napkin of claim 1, wherein said side edges, said cover and said baffle are bonded together to form an edge seal.

9. The sanitary napkin of claim 1, wherein at least one of said cover and said baffle extend laterally beyond said absorbent to define said side edges.

10. The sanitary napkin of claim 8, wherein said garment attachment panels are attached to said baffle side of said edge seal.

* * * * *